US010098722B2

(12) United States Patent
Shalaby et al.

(10) Patent No.: US 10,098,722 B2
(45) Date of Patent: *Oct. 16, 2018

(54) ABSORBABLE/BIODEGRADABLE COMPOSITE YARN CONSTRUCTS AND APPLICATIONS THEREOF

(71) Applicant: Poly-Med, Inc., Anderson, SC (US)

(72) Inventors: Shalaby W. Shalaby, Anderson, SC (US); Shawn Peniston, Easley, SC (US); Scott Taylor, Pendleton, SC (US); Douglas D. Greene, Easley, SC (US)

(73) Assignee: Poly-Med, Inc., Anderson, SC (US)

( * ) Notice: Subject to any disclaimer, the term of this patent is extended or adjusted under 35 U.S.C. 154(b) by 268 days.

This patent is subject to a terminal disclaimer.

(21) Appl. No.: 14/262,845

(22) Filed: Apr. 28, 2014

(65) Prior Publication Data

US 2014/0309667 A1 Oct. 16, 2014

(51) Int. Cl.
*A61B 17/08* (2006.01)
*A61F 2/00* (2006.01)
*A61L 17/14* (2006.01)
*D04B 21/12* (2006.01)
*A61L 17/00* (2006.01)
*A61L 17/10* (2006.01)
*A61L 17/12* (2006.01)
*A61L 31/10* (2006.01)
*A61L 31/12* (2006.01)
*D04C 1/12* (2006.01)

(52) U.S. Cl.
CPC .......... *A61F 2/0063* (2013.01); *A61L 17/005* (2013.01); *A61L 17/105* (2013.01); *A61L 17/12* (2013.01); *A61L 17/145* (2013.01); *A61L 31/10* (2013.01); *A61L 31/129* (2013.01); *D04B 21/12* (2013.01); *D04C 1/12* (2013.01); *A61F 2002/0068* (2013.01); *A61F 2210/0004* (2013.01); *A61F 2250/003* (2013.01); *A61L 2430/00* (2013.01); *D10B 2509/04* (2013.01); *D10B 2509/08* (2013.01)

(58) Field of Classification Search
CPC .... A61F 2/0031; A61F 2/0045; A61F 2/0063; A61F 2002/0068; A61F 2002/0072
See application file for complete search history.

(56) References Cited

U.S. PATENT DOCUMENTS

| | | | |
|---|---|---|---|
| 5,143,082 A | 9/1992 | Kindberg et al. | |
| 5,217,495 A | 6/1993 | Kaplan et al. | |
| 5,458,636 A * | 10/1995 | Brancato | A61F 2/0063 606/151 |
| 6,014,939 A | 1/2000 | Gusmeri et al. | |
| 6,063,105 A | 5/2000 | Totakura | |
| 6,319,264 B1 * | 11/2001 | Tormala | A61F 2/0063 606/151 |
| 6,342,065 B1 | 1/2002 | Shalaby | |
| 6,350,284 B1 | 2/2002 | Törmälä et al. | |
| 6,391,037 B1 * | 5/2002 | Greenhalgh | A61B 17/12022 606/151 |
| 6,398,814 B1 | 6/2002 | Paasimaa et al. | |
| 6,462,169 B1 | 10/2002 | Shalaby | |
| 6,498,229 B1 | 12/2002 | Shalaby | |
| 8,709,023 B2 * | 4/2014 | Shalaby | A61F 2/0063 606/151 |
| 2002/0120291 A1 | 8/2002 | Shalaby | |
| 2003/0040809 A1 | 2/2003 | Goldmann et al. | |
| 2004/0028583 A1 | 2/2004 | Hedman | |
| 2007/0198040 A1 * | 8/2007 | Buevich | A61F 2/0063 606/151 |
| 2008/0306494 A1 * | 12/2008 | Magnusson | A61F 2/0063 606/151 |

FOREIGN PATENT DOCUMENTS

| | | |
|---|---|---|
| CN | 1502992 | 6/2004 |
| CN | 200680013813.8 | 4/2006 |
| CN | 201410126879.4 | 4/2006 |
| CN | 200710181706.2 | 10/2007 |
| EP | 06750856.4 | 4/2006 |
| EP | 07020990.3 | 10/2007 |
| JP | 2000 279433 | 10/2000 |
| JP | 2002 210523 | 7/2002 |
| JP | 2004-523291 | 8/2004 |
| JP | 2008-508944 | 4/2006 |
| JP | 2007-277732 | 10/2007 |
| WO | 9951163 A1 | 10/1999 |
| WO | WO 1999/51163 | 10/1999 |
| WO | WO 2002/0120291 | 8/2002 |
| WO | WO 2003/092758 | 11/2003 |
| WO | 2004028583 A2 | 4/2004 |
| WO | WO 2004/028583 | 4/2004 |
| WO | PCT/US2006/014939 | 4/2006 |
| WO | WO 2006/116000 | 11/2006 |

OTHER PUBLICATIONS

U.S. Appl. No. 60/674,826, filed Apr. 20, 2005, Shalaby.
U.S. Appl. No. 11/886,370 (U.S. Pat. No. 8,585,772), filed Apr. 20, 2006 (Nov. 19, 2013), Shalaby.
U.S. Appl. No. 11/879,357 (U.S. Pat. No. 8,709,023), filed Jul. 17, 2007 (Apr. 29, 2014), Shalaby.
U.S. Appl. No. 14/262,845 (2014/0309667), filed Jul. 17, 2007 (Oct. 16, 2014), Shalaby.

(Continued)

*Primary Examiner* — Melanie Tyson
(74) *Attorney, Agent, or Firm* — BioMed IP

(57) ABSTRACT

Absorbable composite medical devices such as surgical meshes and braided sutures, which display two or more absorption/biodegradation and breaking strength retention profiles and exhibit unique properties in different clinical settings, are made using combinations of at least two types of yarns having distinctly different physicochemical and biological properties and incorporate in the subject construct special designs to provide a range of unique properties as clinically useful implants.

17 Claims, No Drawings

(56) References Cited

OTHER PUBLICATIONS

U.S. Appl. No. 14/795,922 (2015/0305848), filed Jul. 17, 2007 (Oct. 29, 2015), Shalaby.
(U.S. Appl. No. 14/795,922) Non-Final Office Action dated Dec. 11, 2017.
(U.S. Appl. No. 14/795,922) Response to Restriction Requirement filed Oct. 30, 2017.
(U.S. Appl. No. 14/795,922) Restriction Requirement dated Aug. 29, 2017.
(U.S. Appl. No. 14/795,922) Preliminary Amendment dated Jul. 10, 2015.
(U.S. Appl. No. 11/879,357) (now U.S. Pat. No. 8,709,023) Issue Notification dated Apr. 9, 2014 for.
(U.S. Appl. No. 11/879,357) (now U.S. Pat. No. 8,709,023) Response to Amendment under Rule 312 dated Mar. 14, 2014.
(U.S. Appl. No. 11/879,357) (now U.S. Pat. No. 8,709,023) Issue Fee Payment (PTO-85B) filed Mar. 10, 2014.
(U.S. Appl. No. 11/879,357) (now U.S. Pat. No. 8,709,023) Amendment filed Feb. 24, 2014.
(U.S. Appl. No. 11/879,357) (now U.S. Pat. No. 8,709,023) Notice of Allowance and Fees Due (PTOL-85) dated Dec. 10, 2013.
(U.S. Appl. No. 11/879,357) (now U.S. Pat. No. 8,709,023) Amendment/Request for Reconsideration—After Non-Final Rejection filed Nov. 20, 2013.
(U.S. Appl. No. 11/879,357) (now U.S. Pat. No. 8,709,023) Applicants' Arguments/Remarks Made in an Amendment filed Nov. 20, 2013.
(U.S. Appl. No. 11/879,357) (now U.S. Pat. No. 8,709,023) Non-Final Rejection dated May 30, 2013.
(U.S. Appl. No. 11/879,357) (now U.S. Pat. No. 8,709,023) Request for Continued Examination filed Feb. 18, 2011.
(U.S. Appl. No. 11/879,357) (now U.S. Pat. No. 8,709,023) Amendment with Filing CPA/RCE filed Feb. 18, 2011.
(U.S. Appl. No. 11/879,357) (now U.S. Pat. No. 8,709,023) Final Rejection dated Aug. 19, 2010.
(U.S. Appl. No. 11/879,357) (now U.S. Pat. No. 8,709,023) Amendment/Request for Reconsideration After Non-Final Rejection filed Jun. 24, 2010.
(U.S. Appl. No. 11/879,357) (now U.S. Pat. No. 8,709,023) Non-Final Rejection dated Mar. 24, 2010.
(U.S. Appl. No. 11/879,357) (now U.S. Pat. No. 8,709,023) Response to Restriction Requirement filed Jan. 4, 2010.
(U.S. Appl. No. 11/879,357) (now U.S. Pat. No. 8,709,023) Applicant's Arguments/Remarks made in an Amendment filed Jan. 4, 2010.
(U.S. Appl. No. 11/879,357) (now U.S. Pat. No. 8,709,023) Requirement for Restriction/Election dated Dec. 1, 2009.
(U.S. Appl. No. 11/885,370) (now U.S. Pat. No. 8,585,772) Response to Amendment Under Rule 312 filed Oct. 23, 2013.
(U.S. Appl. No. 11/885,370) (now U.S. Pat. No. 8,585,772) Issue Fee Payment (PTO-85B) and Fee Worksheet (SB06) filed Oct. 15, 2013.
(U.S. Appl. No. 11/885,370) (now U.S. Pat. No. 8,585,772) Amendment After Notice of Allowance under Rule 312 filed Oct. 10, 2013.
(U.S. Appl. No. 11/885,370) (now U.S. Pat. No. 8,585,772) Notice of Allowance and Fees Due (PTOL-85) dated Jul. 15, 2013.
(U.S. Appl. No. 11/885,370) (now U.S. Pat. No. 8,585,772) Amendment Submitted/Entered with Filing of CPA/RCE filed Jun. 6, 2011.
(U.S. Appl. No. 11/885,370) (now U.S. Pat. No. 8,585,772) Final Rejection dated Dec. 6, 2010.
(U.S. Appl. No. 11/885,370) (now U.S. Pat. No. 8,585,772) Amendment/Request for Reconsideration After Non-Final Rejection filed Sep. 13, 2010.
(U.S. Appl. No. 11/885,370) (now U.S. Pat. No. 8,585,772) Non-Final Rejection dated May 19, 2010.
(PCT/US2006/014939) International Preliminary Report on Patentability dated Nov. 13, 2007.
(PCT/US2006/014939) Written Opinion of the International Searching Authority dated Nov. 9, 2007.
(JP Pat App No. 2008-505944) first Office Action.
(JP Pat App No. 2008-505944) second Office Action.
(CN Pat App No. 200680013813.8) first Office Action dated Jan. 22, 2010).
(CN Pat App No. 200680013813.8) second Office Action dated Jul. 6, 2010).
(CN Pat App No. 200680013813.8) third Office Action dated Mar. 29, 2011).
(CN Pat App No. 200680013813.8) fourth Office Action dated Sep. 6, 2011).
(CN Pat App No. 201410126879.4) first Office Action dated Jul. 23, 2015.
(CN Pat App No. 201410126879.4) second Office Action dated Jan. 15, 2016.
(CN Pat App No. 2007101817062) first Office Action dated Dec. 31, 2010).
(CN Pat App No. 2007101817062) second Office Action dated Dec. 31, 2011).
(JP Pat App No. 2007277732) Office Action dated Mar. 12, 2013.
(EP 1874226) Communication dated Jun. 25, 2014.
(EP 07020990.3) Communication from EPO.

\* cited by examiner

ABSORBABLE/BIODEGRADABLE COMPOSITE YARN CONSTRUCTS AND APPLICATIONS THEREOF

This application is a continuation of U.S. patent application Ser. No. 11/879,357, which is now U.S. Pat. No. 8,709,023, issued Apr. 29, 2014, which is a continuation-in-part of PCT Application Serial No. 2006014939 filed Apr. 20, 2006, which claimed the benefit of a prior provisional application U.S. Ser. No. 60/674,826 filed on Apr. 26, 2005, all of which are hereby incorporated herein in their entireties by reference.

FIELD OF THE INVENTION

This invention relates to composite warp knitted and braided constructs, each comprising two types of yarns having significantly different absorption/biodegradation and strength retention profiles to produce warp-knitted meshes and braided sutures exhibiting bimodular changes in their properties when used as surgical implants.

BACKGROUND OF THE INVENTION

Blending of non-absorbable fibers having distinctly different individual physicochemical properties is a well-established practice in the textile industry and is directed toward achieving unique properties based on the constituent fibers in such blends. The most commonly acknowledged examples of these blends include combinations of (1) wool staple yarn and polyethylene terephthalate (PET) continuous multifilament yarn to produce textile fabrics which benefit from the insulating quality of wool and high tensile strength of the polyester; (2) cotton staple yarn and PET continuous multifilament yarn to produce water-absorbing, comfortable (due to cotton), strong (due to PET) fabrics; (3) nylon continuous multifilament yarn and cotton staple yarn to achieve strength and hydrophilicity; and (4) cotton staple yarn and polyurethane continuous monofilament yarn to yield water-absorbing, comfortable elastic fabrics. The concept of blending non-absorbable and absorbable fibers was addressed to a very limited extent in the prior art relative to combining polypropylene (PP) with an absorbable polyester fiber in a few fibrous constructs, such as hernial meshes, to permit tissue ingrowth in the PP component of these meshes and reducing long-term implant mass, as the absorbable fibers lose mass with time. However, the use of totally absorbable/biodegradable blends of two or more yarns to yield fibrous properties that combine those of the constituent yarns is heretofore unknown in the prior art, This provided the incentive to pursue this invention, which deals with totally absorbable/biodegradable composite yarns having at least two fibrous components and their conversion to medical devices, such as sutures and meshes, with modulated, integrated physicochemical and biological properties derived from the constituent yarns and which can be further modified to exhibit specific clinically desired properties.

A key feature of having an absorbable/biodegradable surgical implant comprising at least two differing fibrous components, which, in turn exhibit different absorption and strength retention profiles has been disclosed in the present parent application PCT Serial No. 2006014939. However, these applications did not describe any specifically new construct design of devices such as surgical sutures and hernial meshes, which are responsible for achieving novel clinical properties. Accordingly, this invention is directed to novel construct designs made of fully absorbable/biodegradable surgical sutures, especially those used in slow-healing tissues and surgical meshes such as those used in hernial repair and vaginal tissue reconstruction.

SUMMARY OF THE INVENTION

Generally, the present invention is directed to warp knitted composite meshes and braided composite sutures comprising slow-absorbable/biodegradable and fast-absorbable/biodegradable components, specially sized and constructed to produce surgical devices having unique properties.

One major aspect of this invention is directed to a warp-knitted composite mesh with a minimum area density of 50 g/m$^2$, which includes (a) a slow absorbing/biodegradable multifilament yarn component having individual filament diameter of less than 20 micron; and (b) a fast-absorbing multifilament yarn component having individual filament diameter exceeding 20 micron, wherein the slow-absorbing/biodegradable multifilament component is a segmented copolymer made of molecular chains comprising at least 80 percent of l-lactide-based sequences and the fast-absorbing multifilament component is a segmented polyaxial copolymer made of molecular chains comprising at least 70 percent of glycolide-derived sequences, and wherein the slow-absorbing multifilament component is knitted in a 2-bar sand-fly net pattern and the fast-absorbing multifilament component is knitted in a standard 2-bar marquisette pattern, with all guide bars threaded 1-in and 1-out, using a warp knitting machine. Alternatively, the slow-absorbing multifilament component is knitted in 2-bar full tricot pattern and the fast-absorbing multifilament component yarn is knitted in a standard 2-bar marquisette pattern with all guide bars threaded 1-in and 1-out, using a warp knitting machine.

A clinically important aspect of this invention is the provision of a composite mesh having an area weight of about 130 g/m$^2$ and exhibiting a maximum burst force of at least 250 N and a maximum elongation of less than 10 percent under a 16 N force per cm of mesh width, and when incubated in buffered solution at pH 7.2 and 50° C. for about 2 weeks retains more than 20 percent of its maximum burst force and undergoes at least 12 percent elongation under a force of 16 N per cm of mesh width.

Alternatively, the slow-absorbing/biodegradable multifilament yarn component of the mesh comprises a poly-3-hydroxyalkanoate made of molecular chains consisting of at least 50 percent of 3-hydroxybutyric acid-derived sequences.

This invention also deals with a warp-knitted composite mesh with a minimum area density of 50 g/m$^2$, comprising (a) a slow absorbing/biodegradable multifilament yarn component having individual filament diameter of less than 20 micron; and (b) a fast-absorbing multifilament yarn component having individual filament diameter exceeding 20 micron, wherein said mesh is coated with an absorbable polymer at a coating add-on of at least 0.1 percent based on the uncoated mesh weight. Optionally, the coating comprises a polyaxial copolyester made of molecular chains comprising about 95/5 ε-caprolactone-/glycolide-derived sequences, wherein the coating contains at least 1 bioactive agent selected from those groups known for their antineoplastic, anti-inflammatory, antimicrobial, anesthetic and cell growth-promoting activities.

Another major aspect of this invention deals with a braided composite suture comprising (a) a slow-absorbing/biodegradable multifilament yarn component having individual filament diameter of less than 20 micron, and capable of retaining at least 20 percent of its initial breaking strength when tested individually as a braid and incubated in a phosphate buffer at pH 7.2 and 50° C. for about 2 weeks; and (b) a fast-absorbing/biodegradable multifilament yarn component capable of retaining at least 20 percent of its initial breaking strength when tested individually as a braid and incubated in a phosphate buffer at pH 7.2 and 50° C. for about I day. In one embodiment the slow-absorbing/biodegradable and fast-absorbing/biodegradable multifilament components constitute the core and sheath of the braid, respectively. Alternatively, the slow-absorbing/biodegradable and fast-absorbing/biodegradable multifilament components constitute the sheath and core of the braid, respectively.

In terms of the chemical composition of the composite suture, in one embodiment the slow-absorbing/biodegradable multifilament component comprises a segmented copolymer made of the molecular chains consisting of at least 80 percent of l-lactide-derived sequences and the fast-absorbing/biodegradable multifilament component comprises a segmented polyaxial copolymer made of molecular chains consisting of at least 70 percent of glycolide-derived sequences. Alternatively, the slow absorbable/biodegradable multifilament component comprises silk, or a poly-3-hydroxyalkanoate made of a molecular chain consisting of at least 50 percent of 3-hydroxybutyric acid-derived sequences.

Additional aspects of this invention deal with a braided composite suture as described above coated with an absorbable polymer at a coating add-on of at least 0.1 percent based on the uncoated suture weight. Optionally, the coating comprises a polyaxial copolyester made of molecular chains comprising about 95/5 ε-caprolactone-/glycolide-derived sequences, wherein the coating contains at least one bioactive agent selected from those groups known for their antineoplastic, anti-inflammatory, antimicrobial, anesthetic and cell growth-promoting activities.

DETAILED DESCRIPTION OF PREFERRED EMBODIMENTS

During the first one to two days of introducing an implant in living tissue, an acute inflammation prevails at the implant site. This is manifested as redness, heat, swelling and pain. After about day three, any persistent local inflammatory response to the implant subsides. When a non-absorbable material is implanted, the acute inflammation persists for less than a week and the development of a fibrous connective tissue around the implant progresses for about a month, leading to a generally static, fibrous capsule. A long-term separation of the non-absorbable implant from surrounding tissues by the capsule can lead to complications. Depending on the type of implant site, these complications may (1) increase the risk of infection and (2) interfere with the integration of the implant components with surrounding tissue leading to mechanical instability, as in the case of hernial meshes. On the other hand, if the implant material biodegrades/absorbs over time, the inflammation can be restimulated, incrementally, during the implant residence time period at the site, a feature which can be most desirable in certain applications. These include surgical meshes used in hernial repair, where an incremental restimulation of inflammation can result in controlled and persistent collagen deposition and mechanical integration with the fibrous components of the mesh leading to critically needed mechanical stability. Obviously, one should not expect this to terminate after the first three or four weeks following implantation leading to catastrophic mechanical failure of the mesh. Additionally, the incremental restimulation of inflammation and controlled collagen deposition can be achieved through (1) movement of the mesh components and/or at the mesh-tissue interface; (2) providing continually increased porosity in the mesh to permit progressively increasing facile fibroblast migration; and (3) having structurally stable mesh construction that resists tear and unraveling under dynamic mechanical stresses. And, optimally, the mesh components should be designed to (I) exhibit at least two absorption/strength retention profiles, one that prevails during the first two to four weeks and a second which will be responsible for continued restimulation beyond four weeks; (2) display sufficient mechanical strength and stiffness in the first three to four weeks during which collagen is deposited and the mechanical load at the site commences to be shared between the mesh and surrounding tissue without experiencing premature deformation; (3) accommodate the biomechanical events associated with wound healing and tissue shrinkage, as well as incremental dynamic stresses due to regular motions of active patients, through an incremental increase in the engineering compliance of the mesh; and (4) have a carefully warp-knitted construction that accommodates mechanical changes at the implant site while resisting tearing and breaking/unraveling at the tissue-mesh interface and/or within the mesh construct itself.

In concert with the aforementioned discussion, the present invention addresses the requirements set forth for an optimal mesh. Similarly, it addresses the requirements of an optimum suture that is expected to provide an effective ligation for three to four weeks as well as up to a few months following implantation, as would be required for wound repairs of compromised and slow-healing tissues.

A key general aspect of this invention is directed to a warp-knitted composite mesh with minimum density of 50 g/m$^2$ to ensure having adequate mass and strength to allow anchoring to the natural tissue, using a suture and/or absorbable adhesive, without tearing, unraveling, and/or breaking immediately after placement and during the first few weeks of functional performance. This is to prevent mechanical failure at the tissue-mesh interface or within the mesh components. For anchoring the mesh to the biological site, an absorbable suture of choice will be expected to maintain a strength retention profile that parallels that of a long-lasting component of the composite mesh. Meanwhile, the composite mesh is expected to comprise (1) a slow-absorbing/biodegradable, multifilament yarn component having individual filament diameter of less than 20 micron and preferably less than 15 micron as the main, relatively more flexible matrix of the mesh, which retains a measurable breaking strength for at least six weeks and preferably for more than eight weeks; (2) a fast-absorbing/biodegradable, multifilament yarn component having individual filament diameter of more than 20 micron and preferably exceeding 25 micron, as the minor, relatively less flexible component of the mesh that will be responsible for providing adequate initial rigidity of the mesh, and facile anchoring to the surrounding tissues, while exhibiting a brief breaking strength profile of about two to four weeks—this is to allow the slow-absorbing flexible matrix to become progressively more extensible at about two to four weeks following implantation; and (3) a slow- and fast-absorbing multifilament components in specially designed warp-knitted construction to ensure their mechanical interdependence in terms of load-bearing contributions and ability to anchor to the surrounding tissue using an absorbable tissue adhesive, absorbable suture, or a combination, for example, of an absorbable cyanoacrylate-based adhesive and an absorbable suture—a useful illustration of such warp-knit construction entails knitting the slow-absorbing multifilament component in a 2-bar, sand-fly net pattern and the fast-absorbing component in a standard 2-bar marquisette pattern, with all guide bars threaded 1-in and 1-out in 18 gauge using preferably a Raschel or tricot knitting machine. An alternative composite mesh construction entails knitting the slow-absorbing component using a 2-bar full tricot pattern and the fast-absorbing component using a standard 2-bar marquisette pattern, with all guide bars threaded 1-in and 1-out in 18 gauge. The warp construction can be achieved using other patterns. To improve the initial burst strength of the composite mesh through minimizing the fiber-to-fiber friction coefficient and hence minimize the fraying of the mesh structure, a lubricant coating is applied to the mesh at a level of 0.1 to 10 percent based on the mesh uncoated weight. The absorbable coating can also be used as a carrier for the controlled release of one or more bioactive agents belonging to one or more group of drugs known for their antimicrobial, anti-adhesion, and growth-promoting agents. The ideal coating system can be a crystalline, easy-to-apply, lubricious polymeric system that provides surface lubricity and its composition can be controlled to assist in modulating the absorption/biodegradation profile of the fast-absorbing component at least in the first two weeks following implantation.

Although slow- and fast-absorbable/biodegradable components of the composite are, so far, described as multifilament yarns, which are warped independently, other alternative approaches can be used entailing (I) plying the fast- with the slow-absorbable/biodegradable yarns prior to warping; (2) using one or more additional yarns with a moderate or fast absorption/biodegradation profile; (3) using the fast-absorbing component as a single or two-ply monofilament; (4) using a yarn component based on an elastomeric polymer—this can be in the form of a fast-, moderate- or faster-absorbing monofilament, 2-ply monofilament or multifilament. The use of elastomeric components is expected to accommodate any transient change in stress at the application site at the initial period of implantation when inflammation-induced swelling is encountered. To further modulate the performance of the composite mesh, enzymatically biodegradable, multifilament yarn can be used as the slow-biodegrading component. Such yarns include those based on silk fibroin, poly-4-hydroxyalkanoate, casein, chitosan, soy protein, and similar naturally derived materials with or without chemical modification to modulate their biodegradation and breaking strength retention profiles.

Another key general aspect of this invention is directed to a braided suture comprising at least two absorbable/biodegradable monofilament and/or multifilament yarn components having a range of absorption/biodegradation and breaking strength retention profiles. The rationale for invoking such a diversity in the components constituting the composite braid is practically similar to that noted above for composite mesh, with the exception of the fact that in constructing the braid, there is an additional degree of freedom, namely, having a core and sheath as the basic structural components of the braid. Meanwhile, the braid construction may entail (1) using variable ratios of the core-to-sheath without encountering core popping; (2) having slow-absorbable/biodegradable, multifilament yarn as the core or sheath with the balance of braid consisting of a fast-absorbable/biodegradable multifilament yarn; (3) using elastomeric monofilament, plied monofilament or multifilament yarn as part of the braid construct and preferably in the core at variable levels to impart a controlled level of elasticity—this is to accommodate site swelling during the first few days following suture implantation. The composite suture can be coated to (1) improve its tie-down and handling properties; (2) possibly prolong the breaking strength retention profile; and (3) function as an absorbable carrier for the controlled release of one or more bioagent selected from the groups known for their antimicrobial, anti-adhesion, antithrombogenic, antiproliferative, antineoplastic, anti-inflammatory, and cell growth-promoting activities. The coating can also be used to allow the controlled and timely delivery of anesthetic agents to mediate pains following surgery. A useful feature of using a coating with an antineoplastic agent allows the use of the composite suture in cancer patients to minimize the likelihood of metastasis. Another useful feature is the use of the composite suture in anchoring synthetic vascular graft and perivascular wrap where (1) having two or more absorption/biodegradation profiles can allow accommodating physicomechanical changes at the suture line due to prevailing biological events; and (2) using antithrombogenic and/or antiproliferative agents can be beneficial in maintaining the long-term patency of the graft.

A clinically important aspect of this invention deals with bioactive meshes comprising a coating containing an antineoplastic, anti-inflammatory, and/or antiproliferative agent that allows the use of the composite mesh as vascular wrap in the management of vascular embolism.

Further illustrations of the present invention are provided by the following examples:

EXAMPLE 1

Preparation of Yarns I and H For Composite Mesh Construction

A segmented l-lactide copolymer (P1) prepared by the copolymerization of a mixture of an 88/12 (molar) l-lactide/trimethylene carbonate [following the general polymerization methods described in U.S. Pat. No. 6,342,065 (2002)] was melt-spun using a 20-hole die to produce multifilament Yarn I—this is used as the slow-absorbable/biodegradable component of certain composite meshes. The extruded multifilament yarn was further oriented using a one-stage drawing over a heated Godet at about I00-120° C. prior to its use for knitted mesh construction. Typical properties of Yarn I are shown below, For producing Yarn II, the fast-absorbing/biodegradable component of the composite mesh, a polyaxial, segmented glycolide copolymer (P2), made by ring-opening polymerization of a combination of an 88/7/5 (weight) glycolide/trimethylene carbonate/l-lactide [using the general polymerization method described in U.S. Pat. No. 7,129,319 (2006)] was melt-spun using a 10-hole die and oriented by in-line drawing. Typical properties of Yarn II and the form used in knitting are shown below.

Key properties of Yarns I and II:
Yarn I (2-ply natural yarn)
Fiber Count: 43
Denier Range: 80-100 g/9000 m
Tenacity Range: 1.8 to 4.5 g/denier
Ultimate Elongation: 20-30%
Yarn II (1-ply natural yarn)
Fiber Count: 10
Denier Range: 120-170 g/9000 m
Tenacity Range: 3.5-5.5 g/denier
Ultimate Elongation: 40-70%

EXAMPLE 2

General Method For Composite Mesh Construction

Compositions consisting of Yarns I and II which possess different degradation profiles (one relatively fast degrading and one slow degrading) were constructed using various knitting patterns to construct the desired warp-knitted meshes. Knit constructions were produced using a two-step process of warping yarn onto beams and constructing meshes using a typical Raschel or tricot knitting machine. Various knitting patterns and weight ratios of I to II can and were varied to modulate mechanical properties of the specific mesh. Knit constructions can be made from multifilament yarn, monofilament yarn, or combinations thereof. Knit mesh was heat set or annealed at 120° C. for 1 hour while under constant strain in the wale and course directions. Coating can be applied following annealing to modify the in vivo and/or in vitro characteristics.

EXAMPLE 3

Knitting Process of Mesh Pattern A

The knitting process utilized two warped beams of Yarn 1, threaded on bars 1 and 2, and two warped beams of Yarn II threaded on bars 3 and 4. The knitting machine was equipped with 18-gauge needles. Yarn II was knitted in a 2-bar marquisette pattern and Yarn I was knitted in a 2-bar sand-fly net pattern with all guide bars for each pattern threaded 1-in and 1-out in 18 gauge.

Pattern A (28 courses per inch)
Bar 1—1-0/1-212-3/2-1//2x (1-in, 1-out)
Bar 2—2-3/2-1/1-0/1-2112x (1-in, 1-out)
Bar 3—1-0/0-1//4x (1-in, 1-out)
Bar 4—0-0/3-3//4x (1-in, 1-out)

EXAMPLE 4

Knitting Process of Mesh Pattern-B

The knitting process utilized two warped beams of Yarn I threaded on bars 1 and 2 and two warped beams of Yarn II, threaded on bars 3 and 4. The knitting machine was equipped with 18-gauge needles. Yarn II was knitted in a 2-bar marquisette pattern and Yarn I was knitted in a 2-bar full tricot pattern with all guide bars for each pattern threaded 1-in and 1-out in 18 gauge.

Pattern B (19 courses per inch)
Bar 1—1-0/2-3//4x (1-in, 1-out)
Bar 2—2-3/1-0//4x (1-in, 1-out)
Bar 3—1-0/0-1//4x (1-in, 1-out)
Bar 4—0-0/3-3//4x (1-in, 1-out)

EXAMPLE 5

Characterization and In Vitro Evaluation of Typical Composite Meshes From Example 3

Testing Methods For Meshes from Example 3

Mechanical properties were characterized using the ball burst testing apparatus with physical characteristics based on the ASTM D3787-01 guideline for the fixture geometry (25.4 mm polished steel ball, 4.445 cm diameter inside opening). The mesh was clamped in the fixture without any applied tension and the ball was positioned in the center of the 4.445 mm diameter opening. The ball is then brought down to a position on the mesh such that a 0.1N force is applied. The test is initiated and the ball travels at 2.54 cm/min until failure characterized by the point of maximum load. For each test the following three characteristics were recorded with standard deviation values for n=4 sample sizes:

1) Maximum burst force obtained during the test (N)
2) The extension at the maximum load (mm)
3) The extension at 71N load (mm)

The extension at 71N is used to determine the 16N/cm elongation. The value of 71N is derived from the diameter of the opening (4.445 cm×16N/cm=71N). Initially the mesh has a 44.45 mm diameter and is all in one plane. As the test progresses the ball pushes the mesh downward and creates a cone like shape with the radius of the ball as the tip. Using CAD and curve fitting software a mathematical expression which relates the linear travel of the ball to the change in length of a line that passes under the center of the ball and up to the original 44.45 mm diameter (radial distension) was developed. From this information the percent elongation was determined In vitro conditioned burst strength retention [BSR=(max. load at time point/initial max. load)*100] was conducted using a MTS MiniBionix Universal Tester (model 858) equipped with a burst test apparatus as detailed in ASTM D3787-01. Samples were tested initially, after in vitro conditioning using a 0.1M solution of buffered sodium phosphate at a 12.0pH in 50 mL tubes for 10 days, and after conditioning using a 0.1M solution of buffered sodium phosphate at a 7.2pH in 50 mL tubes for multiple time points of interest. Tubes were placed in racks and incubated at 50° C. under constant orbital-agitation. Samples were removed at predetermined time points for mechanical properties testing (n=3).

Physical Properties of a Typical Warp-knit Composite Mesh From Example 3

TABLE I

Pattern A Warp Knit Composite Mesh Physical Properties

| Knitting Patterrn | Area Weight (g/m$^2$) | Yarn II Content (weight %) |
|---|---|---|
| Pattern A | 132 | 40 |

Mechanical Properties of Meshes From Example 3

TABLE II

Pattern A Warp Knit Composite Mesh Initial Burst Properties

| Sample Description | Max. Burst Force (N) | Elongation at Max Force (mm) | Elongation at 71 N Force (mm) | Elongation at 16 N/cm (%) |
|---|---|---|---|---|
| Pattern A | 356 | 14.6 | 6.8 | 5.2 |

TABLE III

Properties of Pattern A Warp Knit Composite Mesh Following Accelerated In Vitro Conditioning 12 H, 50° C., 10 days

| Sample Description | Max. Burst Force (N) | Elongation at Max Force (mm) | Elongation at 71 N Force (mm) | Elongation at 16 N/cm (%) |
|---|---|---|---|---|
| Pattern A | 194 | 21.5 | 15.8 | 25.6 |

TABLE IV

Properties of Pattern A Warp Knit Composite Mesh Due to Accelerated In Vitro A in (7.2 pH, 50° C.

| In Vitro Duration | BSR (%) | Max. Burst Force | Elongation at Max Force | Elongation at 71 N Force | Elongation at 16 N/cm Force |
|---|---|---|---|---|---|
| 0 days | — | 352 | 14.29 | 6.52 | 4.76 |
| 3 days | 106.3 | 374 | 14.71 | 6.84 | 5.28 |
| 7 days | 44.9 | 158 | 14.24 | 7.92 | 7.14 |
| 11 days | 59.1 | 208 | 18.89 | 13.13 | 18.38 |
| 14 days | 55.7 | 196 | 19.63 | 14.31 | 21.46 |
| 18 days | 52.6 | 185 | 17.98 | 13.20 | 18.56 |
| 21 days | 55.4 | 195 | 18.44 | 13.21 | 18.59 |
| 35 days | 51.4 | 181 | 17.88 | 13.54 | 19.43 |
| 56 days | 36.9 | 130 | 16.37 | 14.01 | 20.66 |

EXAMPLE 6

Characterization and In Vitro Evaluation of Typical Composite Meshes From Example 4

Testing Methods For Meshes From Example 4

Mechanical properties testing was conducted using a MTS MiniBionix Universal Tester (model 858) equipped with a burst test apparatus as detailed in ASTM 1)3787-01. Samples were tested initially and after being conditioned using a 0.1M solution of buffered sodium phosphate at a 12.0pI-1 in 50 mL tubes for 10 days. Tubes were placed in racks and incubated at 50° C. under constant orbital-agitation. Samples were removed at predetermined time points for mechanical properties testing (n=3).

Physical Properties of a Typical Warp-knit Composite Mesh From Example 4

TABLE V

Pattern B Warp Knit Composite Mesh Tabulated Physical Properties

| Knitting Pattern | Area Weight (g/m)² | Yarn B Content (weight %) |
|---|---|---|
| Pattern B | 135 | 31 |

Mesh Resultant Mechanical Properties From Example 4

TABLE VI

Pattern B Warp Knit Composite Mesh Initial Burst Properties

| Sample Description | Max. Burst Force (N) | Elongation at Max Force (mm) | Elongation at 71 N Force (mm) | Elongation at 16 N/cm (°/0) |
|---|---|---|---|---|
| Pattern B | 436 | 16.3 | 7.1 | 5.7 |

TABLE VII

Properties of Pattern B Warp Knit Composite Mesh Following Accelerated In Vitro Conditioning 12 H, 50° C., 10 days,

| Sample Description | Max. Burst Force (N) | Elongation at Max Force (mm) | Elongation at 71 N Force (mm) | Elongation at 16 N/cm (/0) |
|---|---|---|---|---|
| Pattern B | 240 | 19.4 | 13.2 | 18.5 |

EXAMPLE 7

Preparation of Yarn III For Composite Braid Construction

The same polymer precursor, P2, described in Example 1 was used in preparing multifilament Yarn III. The polymer was melt-spun using a 20-hole die to produce multifilament Yarn III, which was further oriented using one-stage drawing over a heated Godet at about 100-120° C., prior to its use in braid construction.

EXAMPLE 8

Construction of Composite Braid SM1-1 Comprising a Yarn I-Core and Yarn III-Sheath Braid SM1-1 was prepared using a 4-carrier core of Yarn I as single ply and 8-carrier Yarn III as 3-ply. The braid was hot-stretched to about 5-10 percent of its initial length using heated air at about 90° C. to tighten the braid construction. The strained braid was then annealed at 110° C. for 1 hour to yield a braided suture having about 110 ppi and a diameter of about 0.35 MM.

EXAMPLE 9

Construction of Composite Braid SM1-2 Comprising a Yarn III-Core and Yarn I-Sheath Braid SM1-2 was prepared using a 6-carrier core of Yarn III as single ply and 16-carrier sheath of Yarn I as single ply. The braid was hot stretched and annealed as described in Example 8 to yield a braided suture having about 50 ppi and a diameter of about 0.36.

EXAMPLE 10

In Vitro and In Vivo Evaluation of Braids SM1-1 and SM1-2 Suture Properties

The braids were sterilized with ethylene oxides and tested for their (1) initial physical properties; (2) accelerated in vitro breaking strength retention profile at pH 7.2 and 50° C.; and (3) in vivo breaking strength retention using a subcutaneous rat model. The results of the in vitro and in vivo evaluation are summarized in Table VIII.

TABLE VIII

In Vitro and In Vivo Properties of Composite Braids SMI-1 and SMI-2

| Experiment | | Braid SMI-1 | Braid SMI-2 |
|---|---|---|---|
| Physical Properties: | | | |
| Diameter, mm | | 0.35 | 0.36 |
| Initial Strength, Kpsi (N) | | 54.4 (36.1) | 52.4 (36.7) |
| Elongation, % | | 45 | 41 |
| Knot Max. Load, N | | 24.7 | 23.7 |
| In vitro Breaking Strength Retention (BSR) at | | 85, 50, 24 | 81, 80, — |
| In-Vivo BSR at Percent at | Weeks 1 and 2 | 21, 19 | 76, 76 |
| | Weeks 2 and 3 | 43, 25 | 81, 77 |

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. An absorbable/biodegradable surgical implant comprising:
    a warp-knitted composite mesh, the mesh comprising:
    at least first and second fibrous components, the fibrous components having differing absorption profiles and differing strength retention profiles in a biological environment;
    wherein the first fibrous component comprises a slow-absorbing, biodegradable multifilament yarn component having an individual filament diameter of less than about 20 microns, the slow-absorbing yarn component comprising a segmented copolymer comprising at least 80 percent of l-lactide-based sequences;
    wherein the second fibrous component comprises a fast-absorbing multifilament yarn component having an individual filament diameter of greater than 20 microns, the fast-absorbing yarn component comprising a segmented polyaxial copolymer comprising at least 70 percent of glycolide-based sequences;
    wherein the composite mesh is knit in a four bar pattern wherein the slow-absorbing yarn component is knit in a two bar pattern and the fast-absorbing yarn component is knit in a two bar pattern and are initially mechanically interdependent, and
    wherein upon incubation in a buffered solution at a pH of 7.2 at about 50° C. for about 2 weeks the composite mesh retains more than 20 percent of its maximum burst force and undergoes at least 12 percent elongation under a force of 16 N per cm of mesh width.

2. The implant of claim 1 wherein the slow-absorbing yarn component is knitted in a 2-bar sand-fly net pattern and the fast-absorbing yarn component is knitted in a standard 2-bar marquisette pattern, with all guide bars threaded 1-in and 1-out, using a warp knitting machine.

3. The implant of claim 2 having an area weight of about 130 g/m$^2$ and exhibiting a maximum burst force of at least 250 N and a maximum elongation of less than 10 percent under a 16 N force per cm of mesh width.

4. The implant of claim 2 wherein the segmented copolymer of the slow-absorbing, biodegradable multifilament yarn component is made from an 88/12 (molar) mixture of l-lactide/trimethylene carbonate and the segmented polyaxial copolymer of the fast-absorbing, biodegradable multifilament yarn component is made by copolymerization of a combination of 88/7/5 (weight) glycolide/trimethylene carbonate/l-lactide.

5. The implant of claim 4 wherein the slow-absorbing biodegradable multifilament yarn component has a denier range of 80-100 g/9000 m, a tenacity range of 1.8-4.5 g/denier, and an ultimate elongation of 20-30% and the fast-absorbing biodegradable multifilament yarn component has a denier range of 120-170 g/9000 m, a tenacity range of 3.5-5.5 g/denier, and an ultimate elongation of 40-70%.

6. The implant of claim 4 wherein the slow absorbing yarn component is on Bar 1 and Bar 2, the fast-absorbing yarn component is on Bar 3 and Bar 4, and the mesh is knit in the following pattern at 28 courses per inch: Bar 1-1-0/1-2/2-3/2-1//2 times; Bar 2-2-3/2-1/1-0/1-2//2 times; Bar 3-1-0/0-1//4 times; Bar 4-0-0/3-3//4 times.

7. The implant of claim 2 wherein the slow absorbing yarn component is on Bar 1 and Bar 2, the fast-absorbing yarn component is on Bar 3 and Bar 4, and the mesh is knit in the following pattern at 28 courses per inch: Bar 1-1-0/1-2/2-3/2-1/12 times; Bar 2-2-3/2-1/1-0/1-2/12 times; Bar 3-1-0/0-1//4 times; Bar 4-0-0/3-3//4 times.

8. The implant of claim 2 wherein the slow absorbing yarn component is on Bar 1 and Bar 2, the fast-absorbing yarn component is on Bar 3 and Bar 4, and the mesh is knit in the following pattern at 19 courses per inch: Bar 1-1-0/2-3//4 times; Bar 2-2-3/1-0//4times; Bar 3-1-0/0-1//4 times; Bar 4-0-0/3-3//4 times.

9. The implant of claim 1 wherein the slow-absorbing yarn component is knitted in a 2-bar full tricot net pattern and the fast-absorbing yarn component is knitted in a standard 2-bar marquisette net pattern with all guide bars threaded 1-in and 1-out, using a warp knitting machine.

10. The implant of claim 9 having an area weight of about 130 g/m$^2$ and exhibiting a maximum burst force of at least 250 N and a maximum elongation of less than 10 percent under a 16 N force per cm of mesh width.

11. The implant of claim 9 wherein the segmented copolymer of the slow-absorbing, biodegradable multifilament yarn component is made from an 88/12 (molar) mixture of l-lactide/trimethylene carbonate and the segmented polyaxial copolymer of the fast-absorbing, biodegradable multifilament yarn component is made by copolymerization of a combination of 88/7/5 (weight) glycolide/trimethylene carbonate/l-lactide.

12. The implant of claim 11 wherein the slow-absorbing biodegradable multifilament yarn component has a denier range of 80-100 g/9000 m, a tenacity range of 1.8-4.5 g/denier, and an ultimate elongation of 20-30% and the fast-absorbing biodegradable multifilament yarn component has a denier range of 120-170 g/9000 m, a tenacity range of 3.5-5.5 g/denier, and an ultimate elongation of 40-70%.

13. The implant of claim 11 wherein the slow absorbing yarn component is on Bar 1 and Bar 2, the fast-absorbing yarn component is on Bar 3 and Bar 4, and the mesh is knit in the following pattern at 19 courses per inch: Bar 1-1-0/2-3//4 times; Bar 2-2-3/1-0//4 times; Bar 3-1-0/0-1//4 times.; Bar 4-0-0/3-3//4 times.

14. The implant of claim 1 wherein the mesh is coated with an absorbable polymer coating, the coating present in an amount comprising at least 0.1 percent of the uncoated mesh weight.

15. The implant of claim 14 wherein the absorbable polymer coating comprises a polyaxial copolyester comprising molecular chains of about 95/5 γ-caprolactone-/glycolide-derived sequences.

16. The implant of claim 14 wherein the absorbable polymer coating contains at least one bioactive agent selected from antineoplastic agents, anti-inflammatory agents, antimicrobial agents, anesthetic agents and cell-growth promoting areas.

17. The implant of claim 1 wherein the segmented copolymer of the slow-absorbing, biodegradable multifilament yarn component is made from an 88/12 (molar) mixture of l-lactide/trimethylene carbonate and the segmented polyaxial copolymer of the fast-absorbing, biodegradable multifilament yarn component is made by copolymerization of a combination of 88/7/5 (weight) glycolide/trimethylene carbonate/l-lactide.

* * * * *